(12) United States Patent
Korsten et al.

(10) Patent No.: US 7,635,709 B2
(45) Date of Patent: Dec. 22, 2009

(54) COMPOSITIONS AND METHODS FOR BOWEL CARE IN INDIVIDUALS WITH CHRONIC INTESTINAL PSEUDO-OBSTRUCTION

(75) Inventors: Mark Korsten, Hastings-on-Hudson, NY (US); William A. Bauman, New Rochelle, NY (US)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 713 days.

(21) Appl. No.: 10/672,241

(22) Filed: Sep. 25, 2003

(65) Prior Publication Data

US 2004/0082644 A1     Apr. 29, 2004

Related U.S. Application Data

(60) Provisional application No. 60/413,456, filed on Sep. 26, 2002.

(51) Int. Cl.
*A61K 31/14* (2006.01)
*A61K 31/40* (2006.01)
*A61K 31/44* (2006.01)

(52) U.S. Cl. .................. 514/411; 514/304; 514/423; 514/642

(58) Field of Classification Search ............ 514/642, 514/411, 304, 423
See application file for complete search history.

(56) References Cited

U.S. PATENT DOCUMENTS

| 5,362,756 A | 11/1994 | Riviere et al. |
| 6,469,030 B2 | 10/2002 | Farrar et al. |

FOREIGN PATENT DOCUMENTS

EP     0140434 A2 *  5/1985

OTHER PUBLICATIONS

Vavilala et al. Neostigmine for acute colonic pseudo-obstruction. New England Journal of Medicine, 1999 vol. 341, No. 21, pp. 1622-1623.*

Calvet et al., "Repeated Neostigmine Dosage as Palliative Treatment for Chronic Colonic Pseudo-Obstruction in a Patient with Autonomic Paraneoplastic Neuropathy," *The American Journal of Gastroenterology*, vol. 98, No. 3, pp. 708-709, 2003.
Child, "Glycopyrrolate and the Bowel," *Anaesthesia*, vol. 39, No. 5, pp. 495-496, 1984.
Child, "Prevention of Neostigmine-Induced Colonic Activity," *Anaethesia*, vol. 39, pp. 1083-1085, 1984.
Fajardo, et al., "Decreased Colonic Motility in Persons With Chronic Spinal Cord Injury," *The American Journal of Gastroenterology*, vol. 98, No. 1, pp. 128-134, 2003.
Mehan et al., "Comparison of Recovery in Patients Receiving Atropine-Neostigmine or Glycopyrrolate-Neostigmine for Reversal of Neuromuscular Block," *Ind. J. Anaesth.*, vol. 38, pp. 234-238, 1990.
Ponec et al., "Neostigmine for the Treatment of Acute Colonic Pseudo-Obstruction," *The New England Journal of Medicine*, vol. 341, No. 3, pp. 137-141, 1999.
Korsten et al., "Infusion of Neostigmine-Glycopyrrolate for Bowel Evacuation in Persons with Spinal Cord Injury," *Am. J. Gastroenterology*, 100:1560-1565, 2005.
Nelson and Fine, "Bowel Elimination and Continence," Nursing Practice Related to Spinal Cord Injury and Disorders: A Core Curriculum, A. Nelson (Ed.), Eastern Paralyzed Veterans Association, Palo Alto, CA, pp. 203-223, 2001.
Stiens et al., "Neurogenic Bowel Dysfunction After Spinal Cord Injury: Clinical Evaluation and Rehabilitative Management," *Arch. Phys. Med. Rehabil.*, 78:S86-S104, 1997.
Stiens et al., "The Gastrointestinal System after Spinal Cord Injury," Spinal Cord Medicine Principles and Practice, V.W. Lin (Ed.), New York, NY, pp. 321-348, 2003.
"Neurogenic Bowel Management in Adults with Spinal Cord Injury," Clinical Practice Guidelines, Spinal Cord Medicine, Consortium for Spinal Cord Medicine, Paralyzed Veterans of America, pp. 1-39, Mar. 1998.

* cited by examiner

*Primary Examiner*—Jennifer M Kim
(74) *Attorney, Agent, or Firm*—Klarquist Sparkman, LLP

(57) ABSTRACT

The present disclosure provides compositions and methods for on-going bowel care for persons with chronic intestinal pseudo-obstruction. The compositions and methods can be administered in a non-clinical setting. The compositions comprise acetylcholinesterase inhibitors for stimulating motility of the bowel in combination with anti-cholinergic agents to counteract the potentially dangerous cardiac side effects of the acetylcholinesterase inhibitor. In some examples, the acetylcholinesterase inhibitor, neostigmine, and the anti-cholinergic agent, glycopyrrolate, are combined in a pharmaceutical composition. Certain examples also provide the frequency and duration of administration of the disclosed drug combinations.

13 Claims, 9 Drawing Sheets

FIG. 1
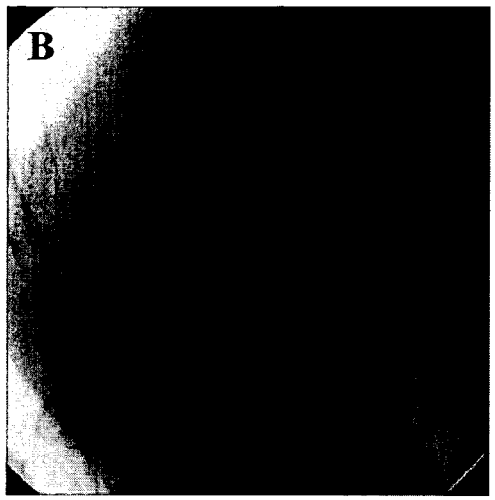
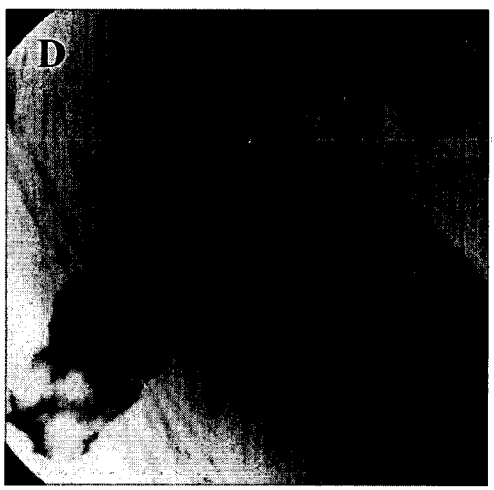
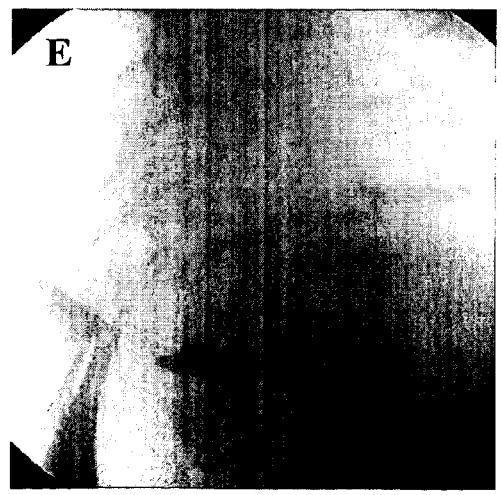

COMPOSITIONS AND METHODS FOR BOWEL CARE IN INDIVIDUALS WITH CHRONIC INTESTINAL PSEUDO-OBSTRUCTION

CROSS REFERENCE TO RELATED APPLICATIONS

This application claims the benefit of U.S. Provisional Application No. 60/413,456, filed Sep. 26, 2002, which is herein incorporated by reference.

FIELD

This disclosure relates to compositions and methods for treating chronic intestinal pseudo-obstruction. In particular, combinations of acetylcholinesterase inhibitors, such as neostigmine, with anti-cholinergic agents, such as glycopyrrolate, are described. Also described are methods of using the disclosed drug combinations for on-going bowel care in individuals with chronic intestinal pseudo-obstruction, such as persons with spinal cord injuries.

BACKGROUND

Normal movement of stool through the colon depends on periodic contractions of the muscles in the wall of the colon that push (or squeeze) fecal matter in the direction of the rectum, which ultimately results in evacuation of the feces. These contractions normally are stimulated by nerves arising from the lower or sacral part of the spinal cord (i.e., S2-4). The effects of these nerves on the colon are generally mediated by a substance called acetylcholine, which causes muscles in the wall of the colon to contract.

The neural control mechanisms of the gastrointestinal (GI) tract are thought to be (or to become) impaired, at least in part, in a number of diseases and medical conditions, e.g., spinal cord injury, amyotrophic lateral sclerosis, spina bifida, multiple sclerosis, Parkinson's disease and dementias, even though the colonic muscles remain intact and capable of responding to acetylcholine. As a result, persons afflicted with these conditions often experience difficulty with bowel functions, including the inability to initiate defecation, straining to defecate, or incomplete evacuation of feces. Because of the chronic nature of the underlying disease, the resulting bowel dysfunction is also chronic and may have a significant negative impact on the subject's quality of life.

Traditional approaches to bowel care for individuals with chronic bowel dysfunction typically involve the periodic administration of laxatives and enemas in combination with digital stimulation of the rectum. These approaches are time consuming and expensive, have unpredictable efficacy, and may cause damage to the bowel. For example, incomplete emptying of the bowel at the time of bowel care increases the likelihood of incontinence, i.e., "accidents." Moreover, the physical trauma of bowel care procedures leads to an increased risk of anorectal problems, especially bleeding hemorrhoids and anal fissures.

Neostigmine is a drug that has long been used by anesthesiologists to reverse the muscle paralysis artificially induced during surgical procedures. Neostigmine is a reversible acetylcholinesterase inhibitor, which blocks the breakdown of the neurotransmitter acetylcholine. This results in an accumulation of acetylcholine in synaptic spaces, which causes (among other things) contractions of the smooth muscles of the bowel.

While smooth muscle contractions in the gut were considered an unwanted side effect by anesthesiologists, other clinicians (e.g., Ponec et al., *New Engl. J. Med.*, 341(3):137-141, 1999) have exploited this neostigmine effect in the treatment of acute colonic pseudo-obstruction. Acute colonic pseudo-obstruction is a relatively rapid onset, intense, short-term condition characterized by bowel distension, constipation, abdominal pain, and the absence of an actual mechanical blockage. Following neostigmine administration for this condition, most patients successfully passed flatus or stool with a corresponding reduction in abdominal distention. However, as expressly recognized by Ponec et al., neostigmine treatment is not without risk. Known side effects of neostigmine include bradycardia (i.e., slowing of the heart rate), excessive pharyngeal and laryngeal secretions, nausea, vomiting, abdominal cramps, and diarrhea. In particular, neostigmine-induced bradycardia can become life threatening and requires close cardiac monitoring in a clinical setting.

Glycopyrrolate is an anti-cholinergic agent (more particularly, a muscarinic antagonist), which blocks neurotransmission by acetylcholine. Glycopyrrolate (or other anti-cholinergic agents, such as atropine) are used by anesthesiologists in the operating room setting or by other clinicians in clinical settings and essentially on emergency basis to counteract the cardiac side effects (e.g., bradycardia) caused by neostigmine.

The potentially life-threatening side effects of neostigmine have historically restricted its usefulness to the clinical setting where the drug recipient is carefully monitored. Even though medications, such as glycopyrrolate, are available to counteract the side effects of neostigmine, those medications have traditionally been administered non-repetitively in the clinical setting only at the time the side effects of neostigmine are induced. For all of these reasons, the routine use of neostigmine for the treatment of a chronic medical condition in a non-clinical setting has been considered unacceptable.

Thus, there remains a need for improved compositions and methods for treating chronic intestinal pseudo-obstruction, such as occurs as a result of spinal cord injury and other medical conditions and disorders.

SUMMARY

Traditional compositions and methods for treatment of chronic intestinal pseudo-obstruction are expensive, uncomfortable, time consuming, difficult to administer and/or may cause damage to the bowel. An easily administered, cost effective treatment that shortened the duration of bowel care without substantial side effects would improve the quality of life for persons with chronic intestinal pseudo-obstruction, who may already have significant morbidity from an underlying chronic disease or condition.

The applicant has surprisingly found that a combination of an acetylcholinesterase inhibitor, such as neostigmine, and an anti-cholinergic agent, such as glycopyrrolate, may be safely administered in repeated doses over a period of time in an on-going bowel care program for subjects with chronic intestinal pseudo-obstruction.

The present disclosure provides compositions and methods for routine bowel care for persons with chronic intestinal pseudo-obstruction. The compositions and methods can be administered on a chronic basis in a non-clinical setting. The compositions comprise acetylcholinesterase inhibitors for stimulating motility of the bowel in combination with anti-cholinergic agents to counteract the potentially dangerous cardiac side effects of the acetylcholinesterase inhibitor. In some examples, the acetylcholinesterase inhibitor, neostigmine, and the anti-cholinergic agent, glycopyrrolate, are combined in a pharmaceutical composition. The described methods provide for administration of the disclosed drug combinations at least once per week.

Certain embodiments of the disclosed methods and compositions can provide advantages such as (i) avoiding incomplete evacuation of the bowels, which may lead to incontinence, (ii) avoiding physical trauma of traditional bowel care methods, and thus reduce the risk of ano-rectal problems such as bleeding hemorrhoids and anal fissures, (iii) providing a more comfortable method of administration, and (iv) providing a relatively rapid therapeutic response.

The foregoing and other features and advantages will become more apparent from the following detailed description of several embodiments, which proceeds with reference to the accompanying figures.

BRIEF DESCRIPTION OF THE FIGURES

FIG. 1 shows digital video fluoroscopy images (panels A-E) of the colons of paraplegic or quadriplegic subjects who had received rectal instillation of a barium-oatmeal paste followed by intravenous administration of a combination of 2 mg neostigmine and 0.4 mg glycopyrrolate. Each of these subjects was having difficulty with evacuation (DWE) at the time of study. The images were collected after a complete response to the drug combination. Panels A, B, C, D, and E represent responses that were adjudged to be 0, 1+, 2+, 3+ and 4+ bowel evacuation scores, respectively.

DETAILED DESCRIPTION

I. Introduction

Figure 2:
FIG. 2 shows a graph of the bowel evacuation scores of thirteen paraplegic or quadriplegic subjects with DWE who received an intravenous bolus of either 2 mg neostigmine alone (black bar) or normal saline (stippled bar).

This specification discloses methods of bowel care for subjects having chronic intestinal pseudo-obstruction. Such methods include chronically administering to the subject a therapeutically effective amount of a drug combination including an acetylcholinesterase inhibitor and an anti-cholinergic agent. In particular embodiments, the chronic administration occurs at least one time per week or at least three times per week over a period of at least one month or over a period of at least six months.

In some embodiments, the acetylcholinesterase inhibitor is neostigmine, physostigmine, ambenonium, pyridostigmine, edrophonium, demecarium, echothiophate, or pralidoxime. In more particular embodiments, the acetylcholinesterase inhibitor is neostigmine. In other examples, the anti-cholinergic agent is glycopyrrolate, atropine, methscopolamine, homatropine, methantheline, propantheline, anisotropine, clidinium, hexocyclium, isopropamide, mepenzolate, oxyphenonium, or tridihexethyl. In more particular examples, the anti-cholinergic agent is glycopyrrolate. In particular methods, the acetylcholinesterase inhibitor is neostigmine and the anti-cholinergic agent is glycopyrrolate.

In some methods, a therapeutically effective amount of the drug combination is about 1 mg to about 2 mg neostigmine and about 0.2 mg to about 0.4 mg glycopyrrolate. In other methods, the therapeutically effective amount of the drug combination is a ratio of neostigmine to glycopyrrolate of about 2.5:1 to about 10:1 by weight, or in more particular methods, of about 5:1 by weight.

In some methods, the intestinal pseudo-obstruction is an effect of spinal cord injury, amyotrophic lateral sclerosis, spina bifida, multiple sclerosis, Parkinson's disease or dementia. In particular methods, the intestinal pseudo-obstruction is an effect of spinal cord injury, such as paraplegia or quadriplegia.

In particular examples of the disclosed methods, the acetylcholinesterase inhibitor and the anti-cholinergic agent are administered at about the same time. In other methods, the anti-cholinergic agent is administered after the acetylcholinesterase inhibitor, for example about 1 to about 10 minutes after the acetylcholinesterase inhibitor.

Examples of suitable methods of administration of the acetylcholinesterase inhibitor or the anti-cholinergic agent include, in each case, intramuscular injection, intravenous injection, rectal suppository, transnasal spray, sublingual tablets, or sublingual drops. In particular methods, the acetylcholinesterase inhibitor and the anti-cholinergic agent are administered by the same method of administration, including intramuscular injection, intravenous injection, rectal suppository, transnasal spray, sublingual tablets, or sublingual drops. In more specific embodiments, the acetylcholinesterase inhibitor and the anti-cholinergic agent are both administered by intramuscular injection or by intravenous injection.

Also disclosed herein are methods of bowel care for a subject with chronic intestinal pseudo-obstruction, which includes identifying a subject having chronic intestinal pseudo-obstruction as an effect of spinal cord injury; co-administering to the subject a therapeutically effective amount of a drug combination comprising about 1 mg to about 2 mg of neostigmine and about 0.2 mg to about 0.4 mg glycopyrrolate. In particular embodiments, the drug combination is chronically administered at least one time per week, such as three times per week, for at least one month, such as for at least six months.

This specification also discloses pharmaceutical compositions including a therapeutically effective amount of a combination of neostigmine and glycopyrrolate in a weight ratio of neostigmine to glycopyrrolate of about 2.5:1 to about 10:1. In certain embodiments, the weight ratio of neostigmine to glycopyrrolate is about 5:1. In other embodiments, the pharmaceutical composition includes about 1 mg to about 2 mg neostigmine and about 0.2 mg to about 0.4 mg glycopyrrolate, or more specifically about 2 mg neostigmine and about 0.4 mg glycopyrrolate.

| II. Abbreviations | |
| --- | --- |
| BMP | beats per minute |
| DWE | difficulty with evacuation |
| GI | gastrointestinal |
| HR | heart rate |
| IM | intramuscular(ly) |
| IV | intravenous(ly) |
| SCI | spinal cord injury |
| SI | spinally intact |

III. Terms

Unless otherwise noted, technical terms are used according to conventional usage. In order to facilitate review of the various embodiments of the invention, the following explanations of specific terms are provided:

Acetylcholine: An acetic acid ester of choline, which serves as a neurotransmitter at the myoneural junctions of striated muscles, at autonomic effector cells innervated by parasympathetic nerves, at the preganglionic synapses of the sympathetic and parasympathetic nervous systems, and at various sites in the central nervous system.

Acetylcholinesterase: An enzyme that catalyzes the cleavage of acetylcholine to choline and acetate. The action of acetylcholinesterase in the synaptic cleft suppresses the neurotransmitter effect of acetylcholine on the post-synaptic cell.

Acetylcholinesterase inhibitor: An agent that interferes with the enzymatic activity of acetylcholinesterase, which results, for example, in local accumulations of acetylcholine in synapses where acetylcholine serves as a neurotransmitter. Representative acetylcholinesterase inhibitors are neostigmine, physostigmine, ambenonium, pyridostigmine, edrophonium, demecarium, echothiophate, or pralidoxime.

Agent: Any substance, including, but not limited to, an antibody, chemical compound, molecule, peptidomimetic, or protein.

Anti-cholinergic agent: Agents that suppress the effects of acetylcholine on the nervous system. Drugs with anti-cholinergic effects inhibit the secretion of acid in the stomach, slow the passage of food through the digestive system, inhibit the production of saliva, sweat, and bronchial secretions, and increase the heart rate and blood pressure. Adverse effects of these drugs include dry mouth, constipation, difficulty urinating, confusion, worsening of glaucoma, blurred vision, and short-term memory problems. Representative anti-cholinergic agents include, for example, anisotropine, atropine, clidinium, dicyclomine, glycopyrrolate, hexocyclium, homatropine, hyoscyamine, ipratropium, isopropamide, mepenzolate, methantheline, methscopolamine, oxyphencyclimine, oxyphenonium, pirenzepine, propantheline, scopolamine, or tridihexethyl.

Bradycardia: A term generally used to mean slowing of the heart rate. Bradycardia may be defined in terms of absolute or relative numbers of heart beats per minute (BPM) or in symptomatic terms. As used herein, "absolute bradycardia" means slowing of the heart rate to less than a specified number of BPM; for example, the slowing of the heart rate to less than about 60 BPM, or to less than about 58 BPM, or to less than about 55 BPM, or to less than about 52 BPM, or to less than about 50 BPM, or to less than about 48 BPM. "Relative bradycardia" means that the baseline heart rate of a particular subject has decreased by a specified number of BPM, or by a specified percentage. The "baseline heart rate" is the heart rate of a subject prior to a perturbation in the subject that affects the heart rate; for example, the heart rate of a subject prior to the administration of an acetylcholinesterase inhibitor, such as, neostigmine, which effects a slowing of the heart rate. In some examples of relative bradycardia, the heart rate in a subject may decreased about 5 BPM below baseline heart rate, or about 7 BPM below baseline heart rate, or about 10 BPM below baseline heart rate, or about 12 BPM below baseline heart rate, or about 15 BPM below baseline heart rate. In other examples of relative bradycardia, the baseline heart rate in a subject may decrease by about 5%, or by about 7%, or by about 10%, or by about 12%, or by about 15%, or by about 20%, or by about 25%, or by about 30%, or by about 35%, or by about 40%, or by about 50%. As used herein, the term "symptomatic bradycardia" is not limited to any specific heart rate or decrease in heart rate; instead, symptomatic bradycardia is describes a slowed heart rate that is accompanied by hypotension (e.g., systolic blood pressure drops by 25% or more), dizziness, extreme fatigue, shortness of breath, and/or fainting spells (i.e., syncope). In some specific examples of symptomatic bradycardia, a subject experiences only hypotension. In some specific examples of symptomatic bradycardia, a subject experiences only dizziness. In other examples of symptomatic bradycardia, a subject experiences hypotension and dizziness. In other examples of symptomatic bradycardia, a subject experiences dizziness and fainting. In still other examples of symptomatic bradycardia, a subject experiences dizziness and shortness of breath. As used herein, "substantial bradycardia" is bradycardia in which the heart rate slows to less than 45 BPM, or in which the heart rate in a subject decreases by 20 BPM below baseline heart rate, or in which the baseline heart rate in a subject decreases by 25% or in which no symptoms of symptomatic bradycardia are observed.

Chronically administering [a drug combination]: The prolonged administration of separate doses of a drug combination to a subject over a period of time. The prolonged administration can occur at regular prescribed intervals or at irregularly intervals (for example, as needed). For example, a chronically administered drug combination may be administered at least twice daily, at least daily, at least five times per week, at least three times per week, at least two times per week, at least one time per week, or at least once every 10 days for at least two administrations, at least 5 administrations, at least 10 administrations, at least 25 administrations, at least 50 administrations, at least 100 administrations, or at least 500 administrations. Accordingly, chronic administration of a drug combination may be continued for weeks, months or years; for example, at least two weeks, at least one month, at least two months, at least three months, at least six months, at least one year, at least five years, or a lifetime of a subject. In particular embodiments of the disclosed methods, a combination of an acetylcholinesterase inhibitor (such as, neostigmine) and an anti-cholinergic agent (such as, glycopyrrolate) are chronically administered at least daily for at least two weeks, or at least three times per week for at least one month, or at least three times per week for at least six months, or at least three times per week for one year, or at least three times per week for a subject's lifetime, or at least five times per week for a subject's lifetime.

Co-administering or co-administration: Administration of two or more agents at substantially the same time in the same or separate dosage forms.

Dementia: An acquired organic mental disorder with loss of intellectual abilities of sufficient severity to interfere with social or occupational functioning. The dysfunction involves, for example, memory, behavior, personality, judgment, attention, spatial relations, language, abstract thought, and other executive functions. The intellectual decline is usually progressive, and initially spares the level of consciousness. Representative dementias include, for example, multi-infarct dementia (as an effect of, for instance, multiple strokes) and Alzheimer disease.

Difficulty with evacuation (or DWE): The inability to initiate defecation, straining to defecate, or incomplete evacuation of fecal matter.

Dosage form: The physical form of a pharmaceutical preparation, which contains amounts of one or more medicaments and, generally, but not necessarily, one or more other ingredients. Dosage forms include, for example, injectables, capsules, liniments, ointments, solutions, powders, tablets, suppositories, transnasal sprays, and sublingual tablets or drops.

Drug combination: A physical and/or functional combination of two or more drugs. The drugs of a drug combination may be included together in a single dosage form, such as in a rectal suppository, an injectable, a transnasal spray, a sublingual tablet or drops, an oral formulation, or a transdermal patch; in which case, the drug combination would most often be administered simultaneously. For example, a drug combination comprising an acetylcholinesterase inhibitor and an anti-cholinergic agent may be combined in a single injectable, which is administered by intravenous or intramuscular injection. Alternatively, the drugs of a drug combination may be provided in different or separate dosage forms, such as in two separate injectables, or in a rectal suppository and an injectable, or in a rectal suppository and a sublingual tablet. Any combination of dosage forms is contemplated as long as the drugs of the drug combination are administered in a manner and at a time that permits the drugs of the combination to treat the chronic intestinal pseudo-obstruction without substantial bradycardia, for example without symptomatic bradycardia. For example, a drug combination comprising an acetylcholinesterase inhibitor and an anti-cholinergic agent may be administered by first injecting the acetylcholinesterase inhibitor intravenously (or intramuscularly) and then, after about 1 to 10 minutes, injecting the anti-cholinergic agent intravenously (or intramuscularly).

Glycopyrrolate (also known as glycopyrronium): An agent that belongs to the class of drugs called anti-cholinergic agents, or more specifically to the class of drugs known as muscarinic antagonists, or even more specifically to the class of drugs known as synthetic, quaternary muscarinic antagonists. The chemical name of one form of glycopyrrolate is pyrrolidinium 3-((cyclopentylhydroxyphenylacetyl)oxy) 1, 1-dimethyl-bromide.

Injectable composition: A pharmaceutically acceptable fluid composition comprising at least one active ingredient, for example, an acetylcholinesterase inhibitor (such as, neostigmine), an anti-cholinergic agent (such as, glycopyrrolate) or a combination of an acetylcholinesterase inhibitor and an anti-cholinergic agent (such as, a combination of neostigmine and glycopyrrolate). The active ingredient is usually dissolved or suspended in a physiologically acceptable carrier, and the composition may additionally comprise one or more non-toxic auxiliary substances, such as emulsifying agents, preservatives, pH buffering agents and the like. Such injectable compositions, which may be used with certain embodiments of the drug combinations described herein, are conventional and appropriate formulations are well known in the art.

Intestinal pseudo-obstruction (or pseudo-obstruction): A condition characterized by signs and symptoms that are usually indicative of intestinal obstruction, such as bowel distension, constipation and abdominal pain, but which occur in the absence of an actual mechanical blockage. "Acute intestinal pseudo-obstruction" is a relatively rapid onset, intense, short-term occurrence of intestinal pseudo-obstruction. "Chronic intestinal psuedo-obstruction" is persistent, recurring intestinal pseudo-obstruction, such as occurs, for example, as a result of spinal cord injury, amyotrophic lateral sclerosis, spina bifida, or multiple sclerosis. Unlike the acute condition, chronic intestinal pseudo-obstruction persistently recurs even after a single bowel evacuation treatment, for example, treatment with the combination of an acetylcholinesterase inhibitor (such as neostigmine) and an anti-cholinergic agent (such as glycopyrrolate). In particular examples, chronic intestinal pseudo-obstruction persists for at least two weeks, and in many instances persists for at least one month, at least six months, at least one year, or even for a lifetime.

Muscarinic antagonist: A class of drugs that bind to, but do not activate, muscarinic cholinergic receptors, and thereby block the actions of endogenous acetycholine or exogenous agonists. Muscarinic antagonists are a class of anti-cholinergic drugs. Muscarinic antagonists can have widespread effects including actions on the iris and ciliary muscle of the eye, the heart and blood vessels, secretions of the respiratory tract, GI system, and salivary glands, GI motility, urinary bladder tone, and the central nervous system. Representative muscarinic antagonists include, for example, anisotropine, atropine, belladonna, clidinium dicyclomine, glycopyrrolate, homatropine, hyoscyamine, hyoscyamine, isopramide, mepenzolate, methantheline, methscopolamine, oxyphencyclimine, pirenzepine, propantheline, scopolamine, and tridihexethyl.

Neostigmine: A drug that belongs to the broader class of agents called acetylcholinesterase inhibitors. One form of the drug, commonly called neostigmine bromide, has the chemical name (m-hydroxyphenyl)trimethylammonium bromide dimethylcarbamate. Another form of the drug, commonly called neostigmine methyl sulfate, has the chemical name (m-hydroxyphenyl) trimethylammonium methyl sulfate dimethylcarbamate.

Parenteral: Administered outside of the intestine, e.g., not via the alimentary tract. Generally, parenteral formulations are those that will be administered through any possible mode except ingestion. This term refers, for example, to injections, whether administered intravenously, intrathecally, intramuscularly, intraperitoneally, or subcutaneously, rectal suppositories, sublingual drops or tablets, and various surface applications including intranasal, intradermal, and topical application. Parenteral administration is preferred for some drugs to avoid degradation of the drug in the gastrointestinal tract, and/or to provide rapid and/or localized absorption or application.

Pharmaceutical agent (or drug): A chemical compound or other composition capable of inducing a desired therapeutic or prophylactic effect when properly administered to a subject.

Spinal cord injury: Any injury of the neural elements within the spinal canal. Spinal cord injury can result from either trauma (e.g., contusion, compression or laceration) or disease to the vertebral column or the spinal cord itself. Most spinal cord injuries are the result of trauma to the vertebral column. These injuries can affect the spinal cord's ability to send and receive messages from the brain to the body systems that control sensory, motor, and autonomic function below the level of injury.

Spinal cord injury may be classified "complete," when the nerve damage obstructs every signal coming from the brain to body parts below the injury, or "incomplete," when only some of the signals are obstructed. In an incomplete injury, the amount and type of message that can pass between the brain and parts of the body will depend on how many nerves have not been damaged. The vertebral level at which the spinal cord injury occurs is often used as a reference point. The closer the injury is to the brain, the greater the loss of function will be.

Persons with paraplegia or quadriplegia are examples of persons with spinal cord injury. A person is said to have paraplegia when he or she has lost feeling and is not able to move the lower parts of the body. Someone with quadriplegia (or, tetraplegia) has lost movement and feeling in both the upper and lower parts of the body.

Subject: Living multicellular vertebrate organisms, a category which includes both human and veterinary subjects for example, mammals, rodents, and birds.

Therapeutically effective amount of a drug combination: The quantity of each of specified agents in a specified drug combination that is sufficient to achieve a desired effect in a subject being treated. For example, this may be the amount of an acetylcholinesterase inhibitor (such as, neostigmine) and the amount of an anti-cholinergic agent (such as, glycopyrrolate) that when combined are sufficient to induce an episode of bowel evacuation with no substantial bradycardia (whether absolute, relative or symptomatic bradycardia) in a subject with chronic intestinal pseudo-obstruction. Specific drug combinations useful for treating chronic intestinal pseudo-obstruction are described herein. Ideally, a therapeutically effective amount of a drug combination includes the amounts of the combined drugs sufficient to induce one episode of bowel evacuation without causing bradycardia or other substantial side effect in the subject being treated. However, the effective amount of a drug combination described herein will be dependent on the subject being treated, the severity of the affliction, and the manner of administration of the therapeutic composition.

An effective amount of a drug combination is intended to be administered so as to induce a single bowel evacuation event; however, it is contemplated that more than one dose may be given to prompt a single bowel evacuation as needed. Regularly occurring doses, for example, at least twice daily, at least daily, at least three times per week, at least two times per week, at least one time per week, at least once every 10 days, at least once every 14 days, or at least once every 20 days are contemplated as needed for bowel care in a particular circumstance. However, the frequency of administration will be dependent on the preparation applied, the subject being treated, the severity and type of the affliction, and the manner of administration of the compound.

Transdermal formulation: A formulation of a drug or drug combination that promotes the absorption of the drug(s) from the skin (also called a skin patch).

Waste disposal repository: Any a container or place where bowel excrement may be collected, for example, diaper, bedpan, colostomy bag, or toilet.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A or B," or "including A and B." Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

IV. Therapeutic Indications and Diagnosis

This disclosure provides methods and compositions for the treatment of chronic intestinal pseudo-obstruction. The subject to be treated is typically a mammal and preferably a human. Diagnosis of chronic intestinal pseudo-obstruction is well within the knowledge of those with skill in the art. Certain clinical features of chronic intestinal pseudo-obstruction and suggested diagnostic measures are described herein; however, one of skill in the art will recognize that other clinical features and diagnostic tests may be useful to identify subjects with chronic intestinal pseudo-obstruction.

The clinical features of chronic intestinal pseudo-obstruction typically include nausea, vomiting, early satiety, abdominal discomfort, distention, bloating, and anorexia, which is persistent and recurring. If stasis and vomiting are significant problems, there may be considerable weight loss, and disturbances of mineral and vitamin stores may result.

One or more of the symptoms of chronic intestinal pseudo-obstruction persist for at least one month, at least two months, at least three months, at least six months, at least one year, at least 5 years, or for a subject's lifetime. Though one of more of the symptoms of chronic intestinal pseudo obstruction may be acutely relieved by a single treatment, at least one symptom characteristic of the condition recurs at least one time and usually many times throughout the subject's lifetime. Following a single treatment to relieve at least one symptom of chronic intestinal pseudo-obstruction, at least one symptom characteristic of the condition recurs, for example, within at least one day of treatment, within at least two days of treatment, within at least three days of treatment, within at least five days of treatment, within at least one week of treatment, within at least two weeks of treatment, or within at least one month of treatment.

In the diagnosis of chronic intestinal pseudo-obstruction, it is usual to rule out the presence of mechanical obstruction of the bowel. Endoscopy (or more specifically, colonoscopy) and/or a small bowel x-ray are representative methods that may be used to exclude mechanical obstruction as a cause of the clinically observed symptoms. A CAT scan of the abdomen may also be useful to determine whether a mechanical bowel obstruction is present.

Diagnosis of chronic intestinal pseudo-obstruction may, but need not, be confirmed by functional tests. For example, a transit profile of the stomach or small bowel, or both, may be performed. These tests may be particularly helpful when scanning is done immediately after ingestion of a radiolabeled meal and then 2, 4, and 6 hours later.

Upper gastrointestinal manometry, using a multilumen tube with sensors strategically placed in the distal stomach and proximal small intestine, may be helpful to differentiate between a neuropathic and myopathic processes resulting in chronic intestinal pseudo-obstruction. Neuropathic conditions are characterized by normal contraction amplitude but uncoordinated contractile activity at the level of the stomach and small intestine. The neuropathic pressure profile shows a reduction in frequency of contractions, with normal contraction amplitude at the level of the stomach (antral hypomotility) or abnormalities in the propagation or coordination of fasting migrating motor complexes or postprandial motor patterns. Myopathic conditions are characterized by markedly reduced contraction amplitude but well-coordinated contractile activity.

In the presence of a neuropathic pattern of motor activity in the small intestine, it may be useful to pursue autonomic function tests. Autonomic testing may identify the presence of sympathetic adrenergic, sympathetic cholinergic, or vagal neuropathies. These abnormalities are revealed by orthostatic hypotension, changes in plasma norepinephrine levels when the patient is in the supine and standing positions, abnormal quantitative sudomotor axon reflex tests, and abnormal tests for vagal function (e.g., the heart interval change during deep breathing and the plasma pancreatic polypeptide response to modified sham feeding).

Chronic intestinal pseudo-obstruction is a clinical condition thought to have multiple etiologies. The particular cause of the condition is not critical to the practice of the methods and use of the compositions described herein, as long as on-going bowel evacuation in the subject may be achieved as described. Chronic intestinal pseudo-obstruction may arise, for example, as a result of neuropathic processes involving enteric and extrinsic nerves, and myopathic processes involving smooth muscle.

Processes involving the extrinsic nervous system include diabetic autonomic neuropathy, amyloidosis, and a paraneoplastic syndrome usually associated with small cell carcinoma of the lung. Surgical vagotomy also disrupts these nerves. Use of certain medications, such as $\alpha_2$-adrenergic agonists, calcium channel blockers, anti-cholinergic drugs, or opiate agents (e.g., tricyclic antidepressants, nifedipine, narcotic analgesics, and antihypertensives such as clonidine), may lead to chronic intestinal pseudo-obstruction.

Disorders of the enteric nervous system that can result in chronic intestinal pseudo-obstruction may be the result of a degenerative, immune, or inflammatory process. Although the cause can only rarely be ascertained, chronic intestinal pseudo-obstruction may be induced by Norwalk virus, cytomegalovirus, and Epstein-Barr virus. Degenerative disorders associated with infiltration of the myenteric plexus with inflammatory cells, including eosinophils, have also been identified. Idiopathic chronic intestinal pseudo-obstruction is thought to occur in patients in whom there is no disturbance of extrinsic neural control and no underlying cause for the enteric neural abnormality.

Disturbances of smooth muscle, including progressive systemic sclerosis and amyloidosis, may result in chronic intestinal psuedo-obstruction. Sometimes dermatomyositis, dystrophia myotonica, and metabolic muscle disorders such as mitochondrial myopathy may be causes.

The methods and compositions described herein are believed to be useful for treating chronic intestinal pseudo-obstruction arising from or in association with the following non-exclusive list of conditions: chronic constipation, obstipation, idiopathic abdominal distention, abdominal pain, abdominal cramps, irritable bowel syndrome, megacolon associated with hypothyroidism, hypomotility of the colon associated with diabetes mellitus, neurological disorders, myopathic disorders, geriatric hypomotility disorders, jejunal-ileal bypass with secondary megacolon, hypomotility associated with cancer chemotherapy, hypomotility associated with severe burns and other major stresses, hypomotility associated with syndromes of depression, Parkinson's disease and other neurodegenerative disorders, post-operative intestinal distension, spinal cord injury, amyotrophic lateral sclerosis, spina bifida, multiple sclerosis, dementia and other pathological conditions.

V. Methods of Use

The methods of the invention comprise administering a therapeutically effective amount of a drug combination comprising an acetylcholinesterase inhibitor and an anti-cholinergic agent to a subject having chronic intestinal pseudo-obstruction.

Although the disclosed methods can be used prophylactically in any subject in a demographic group at significant risk for chronic intestinal pseudo-obstruction, subjects preferably will be selected using more specific criteria, such as a definitive diagnosis of chronic intestinal pseudo-obstruction. For example, treatment can be initiated (and continued as described herein) in a subject having signs and symptoms of chronic intestinal pseudo-obstruction, such as persistent, recurring bowel distension, constipation and abdominal pain in the absence of a mechanical blockage. In particular examples, the clinical picture will suggest chronic intestinal pseudo-obstruction, as in the case of persons with spinal cord injury, neurodegenerative disorders or myopathies.

Acetylcholinesterase inhibitors useful in the disclosed methods are well known in the art. Any acetylcholinesterase inhibitor that can cause smooth muscle contractions in the gut sufficient to induce a single bowel evacuation in a subject without substantial toxic side effects in the subject is contemplated by this disclosure. Representative acetylcholinesterase inhibitors include neostigmine, physostigmine, ambenonium, pyridostigmine, edrophonium, demecarium, echothiophate, and pralidoxime. In certain methods, the acetylcholinesterase inhibitor, neostigmine, is envisioned.

Anti-cholinergic agents useful in the disclosed methods are similarly well known in the art. Any anti-cholinergic agent capable of reducing the cardiac side effects of an acetylcholinesterase inhibitor in a subject without having a substantial effect on the effect of the acetylcholinesterase inhibitor on gut motility in the subject is contemplated. In addition, the anti-cholinergic agent preferably will not have substantial toxic side effects in the subject. Representative anti-cholinergic agents include glycopyrrolate, atropine, methscopolamine, homatropine, methantheline, propantheline, anisotropine, clidinium, hexocyclium, isopropamide, mepenzolate, oxyphenonium, or tridihexethyl. In certain methods, the anti-cholinergic agent, glycopyrrolate, is envisioned.

The disclosed methods contemplate a combination of an acetylcholinesterase inhibitor and an anti-cholinergic agent (individually, a drug, and collectively, drugs). A combination of the drugs envisions a physical combination of the drugs and/or a functional combination of the drugs.

A physical combination of an acetylcholinesterase inhibitor and an anti-cholinergic agent envisions the drugs combined in the same dosage form. For example, some methods contemplate that the drugs will be combined, in the therapeutically effective dosages, in a single injectable composition. In other examples, the drugs will be combined, in the therapeutically effective dosages, in a single rectal suppository or in a transnasal spray or in a sublingual tablet or drop.

The methods described herein also contemplated a functional combination of an acetylcholinesterase inhibitor and an anti-cholinergic agent, which does not necessarily entail a physical combination of the drugs. In these embodiments, the drugs will have separate dosage forms, but will be administered so as to have substantially the same therapeutic effect as if administered in the same dosage form. For example, the drugs may be contained in different dosage forms (such as, two injectables, or an injectable and a suppository, or a suppository and a transnasal spray, or a suppository and a sublingual tablet or drop) and be administered to the subject at approximately the same time (that is, co-administration). Alternatively, the anti-cholinergic agent may be administered anytime after the acetylcholinesterase inhibitor as long as the anti-cholinergic agent is administered in a time frame that is sufficient to counter the cardiac side effects of the acetylcholinesterase inhibitor. For example, the anti-cholinergic agent may be administered between about 1 minute and about 20 minutes, or about 1 minute and about 10 minutes after the acetylcholinesterase inhibitor. More specifically, the anti-cholinergic agent may be administered no more than 1 minute, no more than 2 minutes, no more than 5 minutes, no more than 7 minutes, no more than 10 minutes, no more than 12 minutes, no more than 15 minutes, or no more than 20 minutes after the acetylcholinesterase inhibitor.

The disclosed drug combinations may be administered by any delivery method that provides for delivery of therapeutically effective amounts of the drugs, for example, approximately milligram amounts (e.g., 0.1 mg to 5 mg) of the acetylcholinesterase inhibitor and approximately milligram amounts (e.g., 0.1 mg to 2.5 mg) of the anti-cholinergic agent in a time frame of up to one minute to within several minutes, for example within about 0.5 minute, within about 1 minute, within about 2 minutes, within about 3 minutes, within about 5 minutes, within about 7 minutes, within about 10 minutes or more. The disclosed methods contemplate delivery of the drugs of the disclosed drug combinations, for example, by intravenous injection (including, for instance, by indwelling catheter), by intramuscular injection, by transnasal spray, by sublingual tablet or drops, by rectal suppository, or other fast-acting delivery methods known or developed in the art.

In some embodiments, the disclosed methods provide for routine bowel care for a subject. The frequency of bowel care for each subject will preferably be determined by the subject, the subject's health care providers, or by the subject in consultation with health care providers. For example, routine bowel care may occur at least once each two weeks, at least once every ten days, at least once a week, at least twice a week, at least three times per week, at least four times per week, at least five times per week, at least six times per week, at least daily, or at least twice daily. The duration of treatment for chronic intestinal pseudo-obstruction, such as chronic pseudo-obstruction secondary to spinal cord injury, may be commensurate with the duration of the chronic condition, and in some examples is at least two weeks, at least one month, at least six months, at least one year or for a subject's lifetime.

Therapeutically effective doses of the disclosed drug combinations can be determined by one of skill in the art, with a goal of achieving a bowel evacuation event without substantial bradycardia (for example, symptomatic bradycardia) in a subject, for example, on a scheduled basis compatible with routine bowel care for the subject. Usual dosage ranges for clinically available acetylcholine esterase inhibitors and anti-cholinergic agents may be obtained from the *Physicians' Desk Reference*, 56th Edition (Mountvale, N.J.: Medical Economics Company, Inc., 2002).

An example of a dosage range for the acetylcholinesterase inhibitor, neostigmine, given by injection intravenously, intramuscularly or subcutaneously is, for each mode of administration, up to about 5 mg, up to about 4 mg, or up to about 2 mg in single or divided doses. Other representative dosage ranges for intravenous, intramuscular or subcutaneous injection of neostigmine include, for example, in the range of between about 0.1 mg to about 5 mg IV, between about 0.2 mg to about 4 mg, between about 0.3 mg and about 3 mg, between about 0.5 mg to about 2.0 mg in single or divided doses. In particular examples, dosages of neostigmine include, for example, 2 mg or 4 mg administered by either intravenous or intramuscular injection. In some subjects, for example in children, it may be advantageous to administer the acetylcholinesterase inhibitor on a per kilogram body weight basis; for example, in the range of between about 1.4 µg/kg to about 71 µg/kg, or between about 2.8 µg/kg to about 57 µg/kg, or between about 4.3 µg/kg to about 43 µg/kg, or between about 7.1 µg/kg to about 29 µg/kg administered intravenously or intramuscularly in single or divided doses.

An example of a dosage range for the anti-cholinergic agent, glycopyrrolate, administered intravenously or intramuscularly is, for each mode of administration, up to about 2.5 mg, up to about 1 mg, up to about 0.5 mg, up to about 0.4 mg, or up to about 0.2 mg in single or divided doses. In some examples, glycopyrrolate may be administered by intramuscular injection in the range of 0.001 mg to 0.01 mg/lb body weight in single or divided doses or, for example, at the dosage of 0.002 mg/lb body weight. Other representative dosage ranges for intravenous or intramuscular injection of glycopyrrolate include, for example, in the range of between about 0.1 mg to about 2.5 mg, between about 0.1 mg to about 1 mg, between about 0.1 mg and about 0.5 mg, between about 0.2 mg to about 0.4 mg in single or divided doses. In particular examples, dosages of glycopyrrolate include, for example, 0.2 mg or 0.4 mg administered by either intravenous or intramuscular injection. In some subjects, for example in children, it may be advantageous to administer the anti-cholinergic agent on a per kilogram body weight basis; for example, in the range of between about 1.4 µg/kg to about 38 µg/kg, or between about 1.4 µg/kg to about 15 µg/kg, or between about 1.4 µg/kg to about 7.1 µg/kg, or between about 2.8 µg/kg to about 5.7 µg/kg administered intravenously or intramuscularly in single or divided doses.

In some examples, the acetylcholinesterase inhibitor and anti-cholinergic agent are administered in a particular ratio of acetylcholinesterase inhibitor to anti-cholinergic agent by weight; for example, a ratio of about 2.5:1 to about 10:1, of about 2.5:1 to about 7:1, of about 3:1 to about 5:1. More particularly, in some examples the ratio of acetylcholinesterase inhibitor to anti-cholinergic agent by weight is 5:1 (e.g., 2 mg: 0.4 mg).

As discussed above, the disclosed methods envision that an acetylcholinesterase inhibitor and an anti-cholinergic agent may be (i) co-administered, for example, in the same syringe or in the same rectal suppository or in the same sublingual tablet or drop; or in the same transnasal spray; or (ii) administered at approximately the same time by separate (whether the same or different) modes of administration, for example, in two different syringes, or with one drug administered by injection and the other administered by suppository; or (iii) administered at different times with administration of an acetylcholinesterase inhibitor preceding that of an anti-cholinergic agent.

The specific dose level and frequency of dosage for any particular subject may be varied and will depend upon a variety of factors, including the activity of the specific acetylcholinesterase inhibitor and/or anti-cholinergic agent, the metabolic stability and length of action of those compounds, the age, body weight, general health, sex, diet, mode and time of administration, rate of excretion, drug combination, and severity of the condition of the host undergoing therapy.

The disclosed methods may, but need not, be used in combination with traditional bowel care methods, such as laxatives, enemas and digital stimulation of the rectum. In some examples, digital stimulation of the rectum will be applied concurrent with administration of the disclosed drug combinations or slightly thereafter, for example within about 5 minutes of drug administration, or within about 10 minutes of drug administration, or within about 15 minutes of drug administration, or within about 20 minutes of drug administration, or within about 30 minutes of drug administration. Digital rectal stimulation in combination with the disclosed drug therapy may be particularly useful in patients whose anal sphincters contract in response to neostigmine administration; as may be the case, for example, with some persons with relatively recent spinal cord injuries.

VI. Pharmaceutical Compositions

The disclosed drug combinations may be administered to a subject in the form of a pharmaceutical composition. Pharmaceutical compositions comprising the disclosed drug combinations may be manufactured by means of conventional mixing, dissolving, granulating, levigating, emulsifying, encapsulating, entrapping or lyophilizing processes.

Pharmaceutical compositions may be formulated in conventional manner using one or more physiologically acceptable carriers, diluents, excipients or auxiliaries (such as wetting or emulsifying agents, preservatives, pH buffering agents and the like, for example, sodium acetate or sorbitan monolaurate), which facilitate processing of the active ingredients into preparations that can be used pharmaceutically. Examples of compositions and formulations suitable for pharmaceutical delivery of the agents herein disclosed are described in *Remington's Pharmaceutical Sciences*, by E. W. Martin, Mack Publishing Co., Easton, Pa., 15th Edition, 1975.

Proper formulation is dependent upon the route of administration chosen. The active ingredients may be administered by methods including, but not limited to topical administration, systemic administration, transmucosal administration (including, for example, sublingual tablets or drops and rectal suppositories), oral administration, and administration by inhalation. In some embodiments, the active ingredients are administrated by injections using syringes, spring- or gas-driven syringe devices, or needle-less injector systems. In some other embodiments, the active ingredients are administrated using rectal suppositories.

For topical administration the active ingredients may be formulated as solutions, gels, ointments, creams, suspensions, etc., each of which are well-known in the art.

Systemic formulations include those designed for administration by injection, such as, subcutaneous, intravenous, intramuscular, intrathecal, or intraperitoneal injection, as well as those designed for transdermal, transmucosal, oral or pulmonary administration. For injection, the compounds of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents. Alternatively, the compounds may be in powder form for constitution with a suitable vehicle, for example, sterile pyrogen-free water, before use.

For transmucosal administration, penetrants appropriate to the barrier to be permeated are used in the formulation. Such penetrants are generally known in the art.

For oral administration, the compositions can be readily formulated by combining the active ingredients with pharmaceutically acceptable carriers well known in the art. Such carriers enable the compounds of the invention to be formulated as tablets, pills, capsules, liquids, gels, syrups, slurries, suspensions and the like, for oral ingestion by a patient to be treated. Oral solid formulations, such as powders, capsules and tablets, include suitable excipients and fillers, such as lactose, sucrose, mannitol, sorbitol, maize starch, wheat starch, rice starch, potato starch, gelatin, gum tragacanth, methyl cellulose, hydroxypropylmethyl-cellulose, sodium carboxymethylcellulose, polyvinylpyrrolidone (PVP), and polylcatic/polyglycolic acid, together with granulating agents, and binding agents. If desired, disintegrating agents may be added, such as crosslinked polyvinylpyrrolidone, agar, or alginic acid or a salt thereof, such as sodium alginate. If desired, solid dosage forms may be sugar-coated or enteric-coated using standard techniques.

For oral liquid preparations, such as suspensions, elixirs and solutions, suitable carriers, excipients or diluents, include water, glycols, oils, alcohols, etc. Additionally, flavoring agents, preservatives, coloring agents and the like may be added.

For buccal administration, the active ingredients may take the form of tablets, lozenges, etc., which are formulated in a conventional manner.

For administration by inhalation, the active ingredients for use according to the present disclosure are conveniently delivered in the form of an aerosol spray from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin, for example, for use in an inhaler or insufflator may be formulated containing a powder mix of the compound and a suitable powder base such as lactose or starch.

The active ingredients may also be formulated in rectal or vaginal compositions such as suppositories or retention enemas, for example, containing conventional suppository bases such as cocoa butter or other glycerides.

VII. Kits

The drug combinations disclosed herein can be supplied in the form of kits for use in prevention and/or other treatment of a disorder, condition or diseases (e.g., chronic intestinal pseudo-obstruction). In such a kit, a clinically effective amount of a combination of one or more acetylcholinesterase inhibitor(s) and one or more anti-cholinergic agent(s) is provided in one or more containers. The drug combination may be provided suspended in an aqueous solution or as a freeze-dried or lyophilized powder, for instance. In certain embodiments, the drug combination will be provided in the form of a pharmaceutical composition.

Kits according to this invention can also include instructions, usually written instructions, to assist the user in treating a disorder, condition or disease (e.g., treatment of chronic intestinal pseudo-obstruction) with the combination of one or more acetylcholinesterase inhibitor(s) and one or more anticholinergic agent(s). The instructions can be for use of the drug combination for any of the purposes described herein. Such instructions can optionally be provided on a computer readable medium.

The container(s) in which the drug combination is supplied can be any conventional container that is capable of holding the supplied form, for instance, microfuge tubes, ampoules, suppositories, nasal sprays, or bottles. In some applications, the therapeutic drug combination may be provided in pre-measured single use amounts in individual, typically disposable, ampoules, tubes or equivalent containers.

The amount of a drug combination supplied in the kit can be any appropriate amount, depending for instance on the market to which the product is directed. For instance, if the kit is adapted for clinical or home use, there may be several single-used ampoules or suppositories containing the drug combination which may be used to provide for several treatments.

The following examples are provided to illustrate certain particular features and/or embodiments. These examples should not be construed to limit the invention to the particular features or embodiments described.

EXAMPLES

Example 1

Decreased Colonic Motility Following Spinal Cord Injury

This example describes the effect of food and sleep on colonic motility in persons with spinal cord injury (SCI) as compared to the spinally intact (SI). This example demonstrates that colonic motility is decreased in SCI subjects; thus, such subjects may benefit from a therapeutic approach that increases bowel contractility.

Methods

Eight (8) subjects with SCI (mean age of 59 years, mean duration of injury of 17 years, 5 paraplegics and 3 quadriplegics), and 6 SI subjects (mean age of 57 years) were investigated. Each SCI subject complained of difficulty with evacuation (DWE) at least once in the 6 months preceding testing.

Colonoscopy was performed after routine bowel preparation and all subjects had normal examinations. After colonoscopy, the proximal end of a solid-state pressure transducer catheter (separated by 10 cm) was tethered to the splenic flexure using endoclips (Olympus). The subjects were then allowed to carry out their usual daily activities for at least 24 hours. Data from the catheters were recorded on Gaeltec (Medical Measurements Inc.) portable recorders. The collected data were uploaded to a computer for analysis.

Motility index (as determined by software provided with the Gaeltec portable recorder system) was analyzed 1 hour before breakfast, during breakfast, 1 hour after breakfast, 1 hour prior to sleep, at sleep onset, and 1 hour after sleep onset. The motility index after an average 1 hour of sleep was used as the baseline value for each subject. The Student's t-test was used to determine significant difference.

Results

The motility index determined at 1 hour pre-breakfast (3.6 vs. 9.3, $p<0.01$), during breakfast (4.6 vs. 14.3, $p<0.02$), and 1 hour post-breakfast (3.9 vs. 10.2, $p<0.01$) was significantly less for the SCI group as compared to the SI group. Post prandial colonic response was significant in both groups; however in the SCI group, this response was only evident in the proximal and not the distal leads. Likewise, the motility index determined at 1 hour pre-sleep onset (3.5 vs. 8.7, $p<0.0005$), at sleep onset (1.4 vs. 8.8, $p<0.005$), and 1 hour post-sleep onset (4.5 vs. 17.8, $p<0.001$) was significantly less for the SCI group as compared to the SI group. Sleep-induced depression in motility index was more significant in the SCI group ($p<0.008$). Both groups exhibited significant increases in the motility index during arousal.

This example demonstrates that DWE in SCI subjects is correlated with decreased colonic motility. The example further demonstrates that DWE may be due to phasic postprandial colonic response and a more exaggerated sleep-induced depression of colonic motility in individuals with SCI.

Example 2

Use of Neostigmine and Glycopyrrolate Combination Therapy to Stimulate Bowel Evacuation in Six Subjects with Spinal Cord Injury This example describes the use of a combination of neostigmine and glycopyrrolate to stimulate bowel evacuation in SCI subjects without concomitant bradycardia.

Six (6) subjects with spinal cord injury (both paraplegic and quadriplegic) were tested. Bowel care times were typically 1-2 hours 3 times per week in these individuals. After bowel preparation and establishment of IV access, subjects were transferred to a fluoroscopic imaging table and, while in the supine position, underwent flexible sigmoidoscopy for placement of a solid state motility catheter in the descending colon. The motility apparatus was attached to the colon using a recently described technique that prevents migration of the sensors during the study (Fajardo et al., *Gastrointest. Endosc.*, 51:199-201, 2000). Both the fluoroscopic image and the external end of the catheter were inputted to a system (Kay Elemetrics) that allowed simultaneous real time acquisition of fluoroscopic images and manometric data.

Under fluoroscopic control, the left side of the colon (rectum to splenic flexure) was filled with an oatmeal-barium paste using a bladder syringe and baseline manometric recordings were obtained for 5 minutes. Following these baseline measurements, each subject in random order was given either placebo or a combination of neostigmine (1 mg administered intravenously) and glycopyrrolate (0.2 mg administered intramuscularly). After each administration, manometric recordings were collected for an additional 30 minutes. Total fluoroscopic exposure time was limited to 10 minutes.

At the end of each measurement period, the residual oatmeal-barium paste was aspirated to determine residual "fecal" volume. If a subject failed to have a complete response to 1 mg of neostigmine and 0.2 mg glycopyrrolate, the subject was treated on a different day using a higher dose of neostigmine in the drug combination (i.e., 2 mg neostigmine and 0.4 mg glycopyrrolate administered intramuscularly). The vital signs (i.e., oxygen saturation, pulse and blood pressure) and respiratory status (i.e., auscultation) of each subject were continuously monitored.

Within 10 minutes of administration of the neostigmine-glycopyrrolate mixture, all subjects exhibited high amplitude colonic contractions. In addition, 5 out of 6 of the subjects demonstrated complete evacuation of the barium-oatmeal paste within 25 minutes, most within 15 minutes. No substantial bradycardia was observed in any of the subjects (for example, heart rate did not decrease below 45 BPM in any subject and/or none of the subjects experienced hypotension). The only side effect noted was transient muscle twitching in 2 of the subjects and minimal abdominal cramps in 1 of the subjects.

This example demonstrates that combination therapy with neostigmine and glycopyrrolate can safely stimulate evacuation in a high proportion of individuals with spinal cord injury.

Example 3

Comparison of Bowel Evacuation Response in Thirteen Subjects with Spinal Cord Injury Treated with Neostigmine Alone or a Combination of Neostigmine and Glycopyrrolate This example describes the effect of neostigmine alone and a combination of neostigmine and glycopyrrolate on bowel evacuation in the same subjects using the monitoring methods described in Example 2.

Thirteen (13) persons with SCI (5 quadriplegics, 8 paraplegics) with a mean age of 46 years (range 25-69) and mean duration of injury of 16 years (range 1-31) were treated. None of the subjects had known heart disease and/or history of arrhythmias.

On separate days, subjects were given by IV bolus either (i) 2 mg neostigmine alone, (ii) a combination of 2 mg neostigmine and 0.4 mg glycopyrrolate, or (iii) normal saline. Subjects were blinded to the type of infusion being delivered. The effect of these infusions on bowel evacuation was assessed semi-quantitatively on a scale of 0 (no evacuation) to 4+ (complete evacuation) using video fluoroscopy after rectal instillation of a barium-oatmeal paste having a consistency similar to that of stool. Blood pressure, heart rate and other vital signs were monitored in each subject. In addition, airway resistances were determined in each subject using the forced oscillation technique (as described, for example, in Goldman, *Pulm. Pharmacol. Ther.*, 14(5):341-350, 2001). Total airway resistance was determined using 5 Hz forced oscillations, and central airway resistance was determined using 20 Hz forced oscillations.

FIG. 1 shows examples of the bowel evacuation scoring method. FIG. 1A shows the fluoroscopy image from a subject having no response to the drug combination. This response received a 0 (zero) bowel evacuation score. FIGS. 1B-1E show progressively increasing bowel evacuation responses in different subjects. The responses in FIGS. 1B-1E correspond to bowel evacuation scores of 1+, 2+, 3+, and 4+, respectively.

Figure 3:
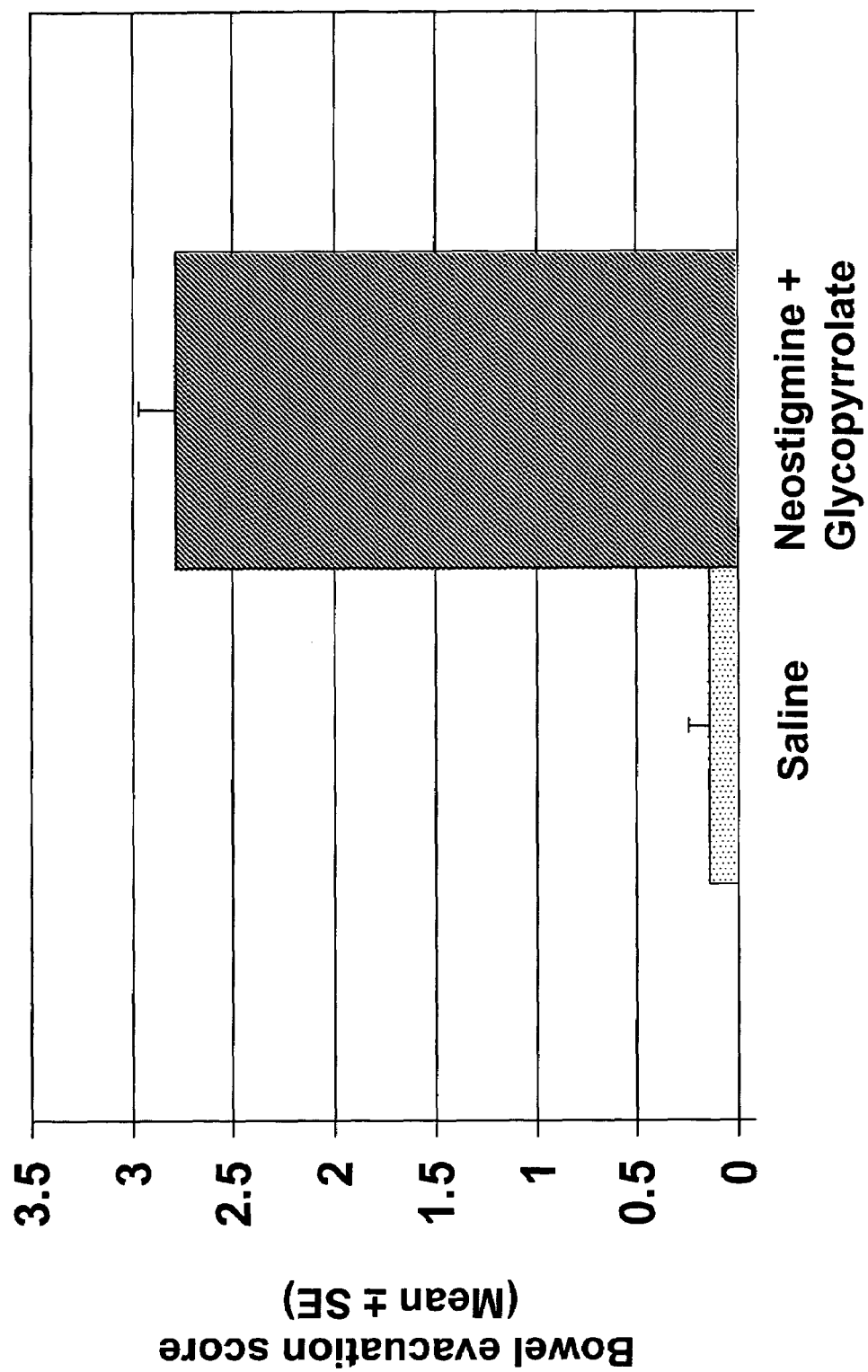
FIG. 3 shows a graph of the bowel evacuation scores of thirteen paraplegic or quadriplegic subjects with DWE who received an intravenous bolus of either a combination of 2 mg neostigmine and 0.4 mg glycopyrrolate (cross-hatched bar) or normal saline (stippled bar).
Figure 4:
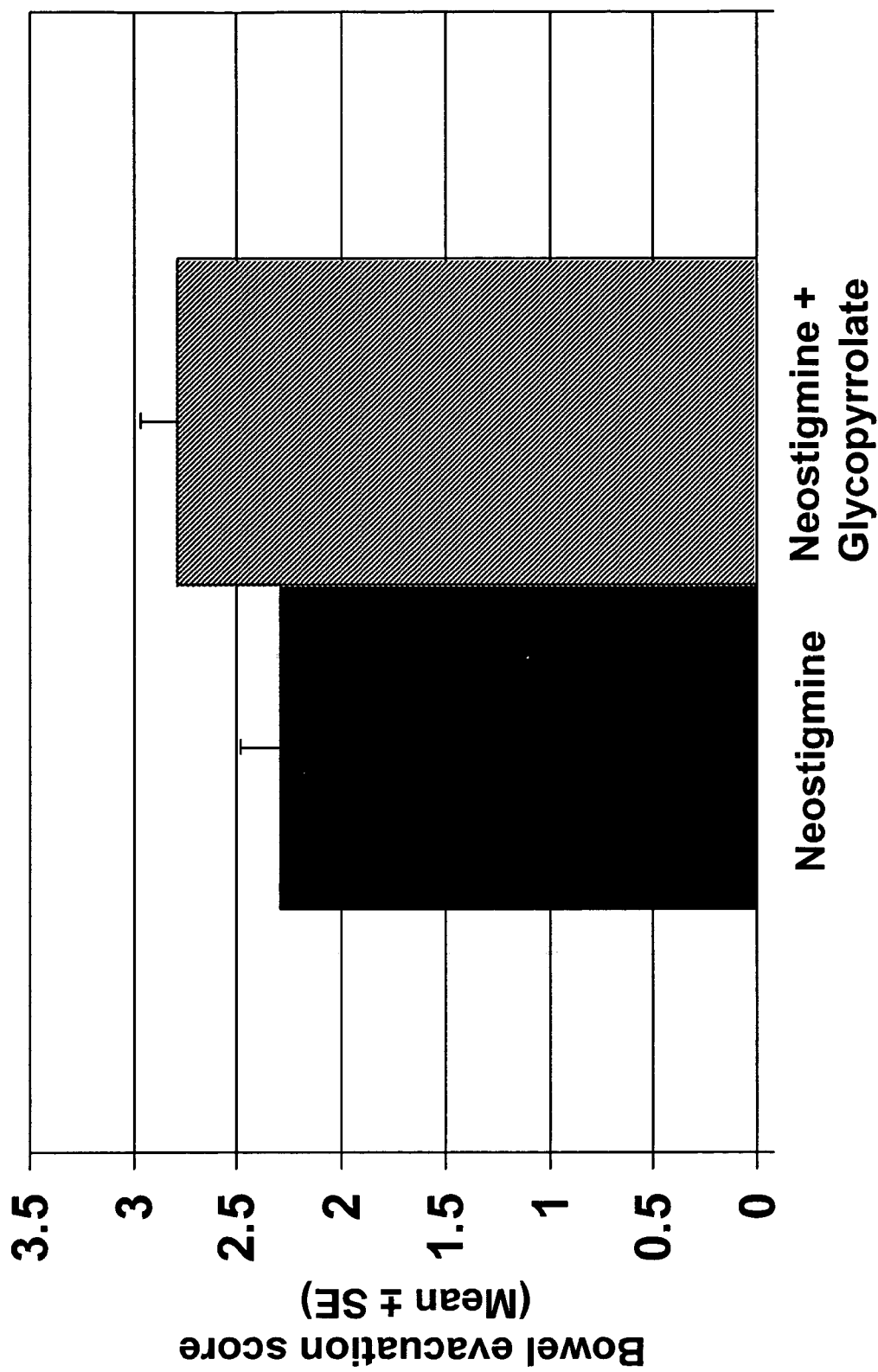
FIG. 4 shows a graph of the bowel evacuation scores of thirteen paraplegic or quadriplegic subjects with DWE who received an intravenous bolus of either 2 mg neostigmine alone (black bar) or a combination of 2 mg neostigmine and 0.4 mg glycopyrrolate (cross-hatched bar).
Figure 5:
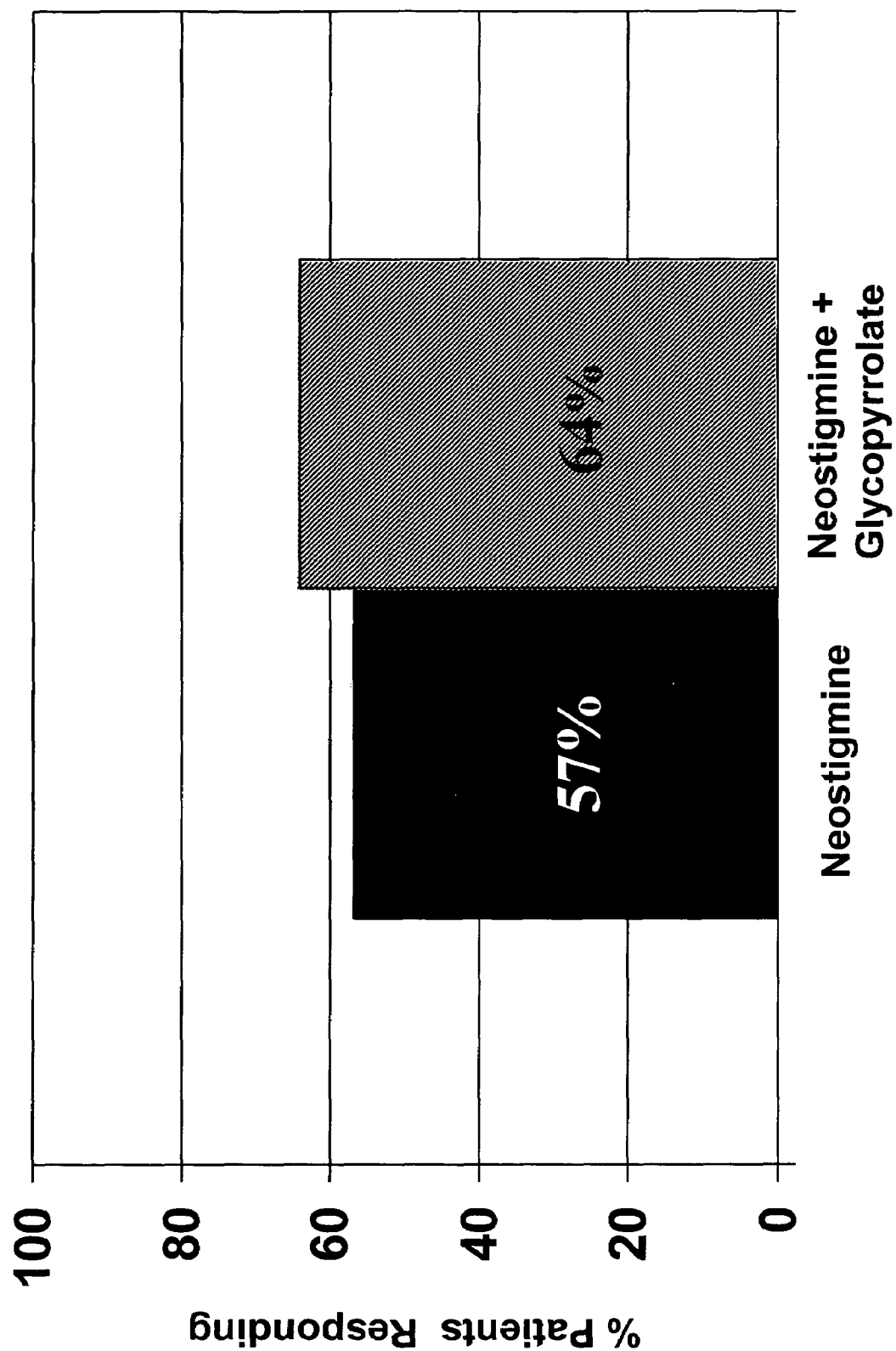
FIG. 5 shows a graph of the percentage of paraplegic or quadriplegic subjects (13 total) having a bowel evacuation score greater than 3 after receiving an intravenous bolus of either 2 mg neostigmine alone (black bar) or a combination of 2 mg neostigmine and 0.4 mg glycopyrrolate (cross-hatched bar).

As shown in FIGS. 2 and 3, mean bowel evacuation score after neostigmine alone was about 2.29 (see FIG. 2), while mean evacuation score after neostigmine and glycopyrrolate was about 2.79 (see FIG. 3). No evacuation was observed over a 20 minute period after normal saline infusion (see FIGS. 2 and 3). Evacuation occurred in the range of 5-20 minutes (mean=11 minutes) post infusion of either neostigmine or the combination of neostigmine and glycopyrrolate. There was no difference between neostigmine or neostigmine and glycopyrrolate in terms of bowel evacuation score (see FIG. 4), the percentage of patients responding (see FIG. 5), or the rapidity of the bowel evacuation response.

Figure 6:
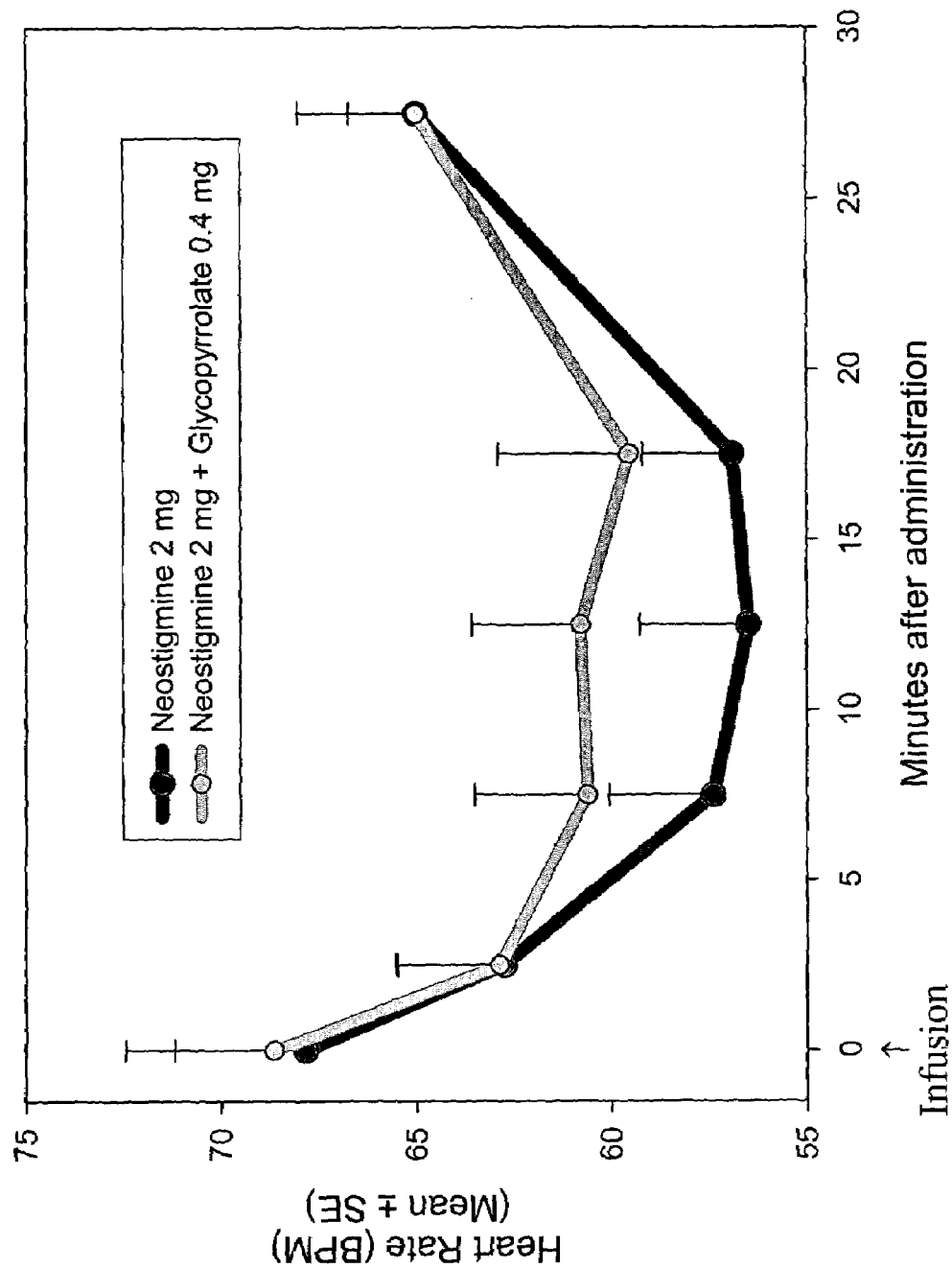
FIG. 6 shows a graph of the time course of the heart rate of thirteen paraplegic or quadriplegic subjects with DWE who received an intravenous bolus of either 2 mg neostigmine alone (black line) or a combination of 2 mg neostigmine and 0.4 mg glycopyrrolate (grey line).
Figure 7:
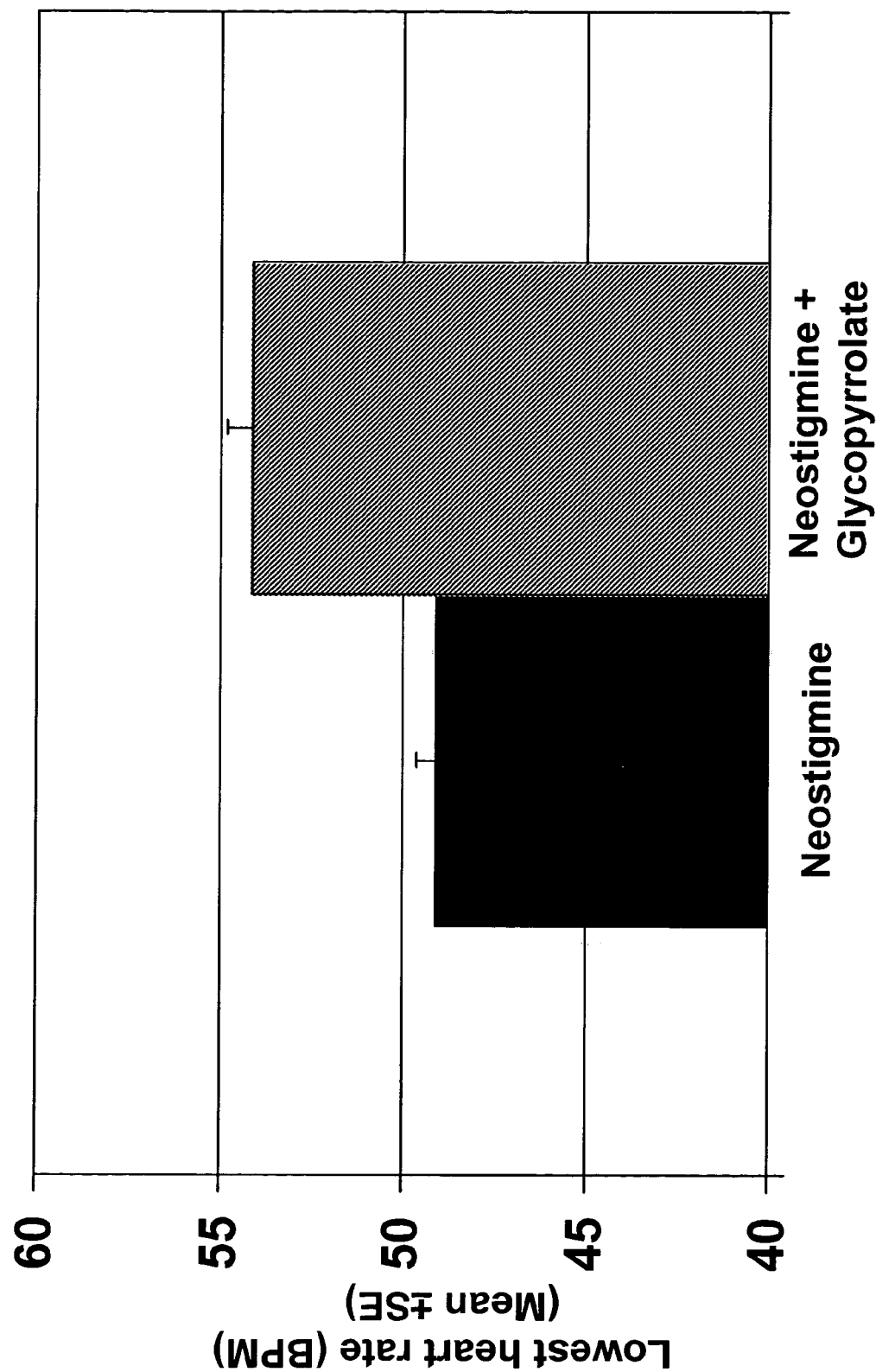
FIG. 7 shows a graph of the lowest heart rate measured in thirteen paraplegic or quadriplegic subjects with DWE who received an intravenous bolus of either 2 mg neostigmine alone (black bar) or a combination of 2 mg neostigmine and 0.4 mg glycopyrrolate (cross-hatched bar).

Quadriplegics and paraplegics did not differ in the likelihood of a response to neostigmine or neostigmine and glycopyrrolate. As shown in FIG. 6, subjects given the combination of neostigmine and glycopyrrolate experienced less bradycardia over a 30-minute time course than did subjects who received neostigmine alone. As shown in FIG. 7, the mean lowest heart rate measured in subjects given neostigmine alone (i.e., about 49 BMP) was significantly less (p=0.02) than that measured the subjects that received the combination of neostigmine and glycopyrrolate (i.e., about 54 BMP). No change in blood pressure was measured after administration of either neostigmine alone or the combination of neostigmine and glycopyrrolate. Other side effects, including muscle twitching, sweating, vague abdominal sensations and salivation, were transient and minimal.

Figure 8:
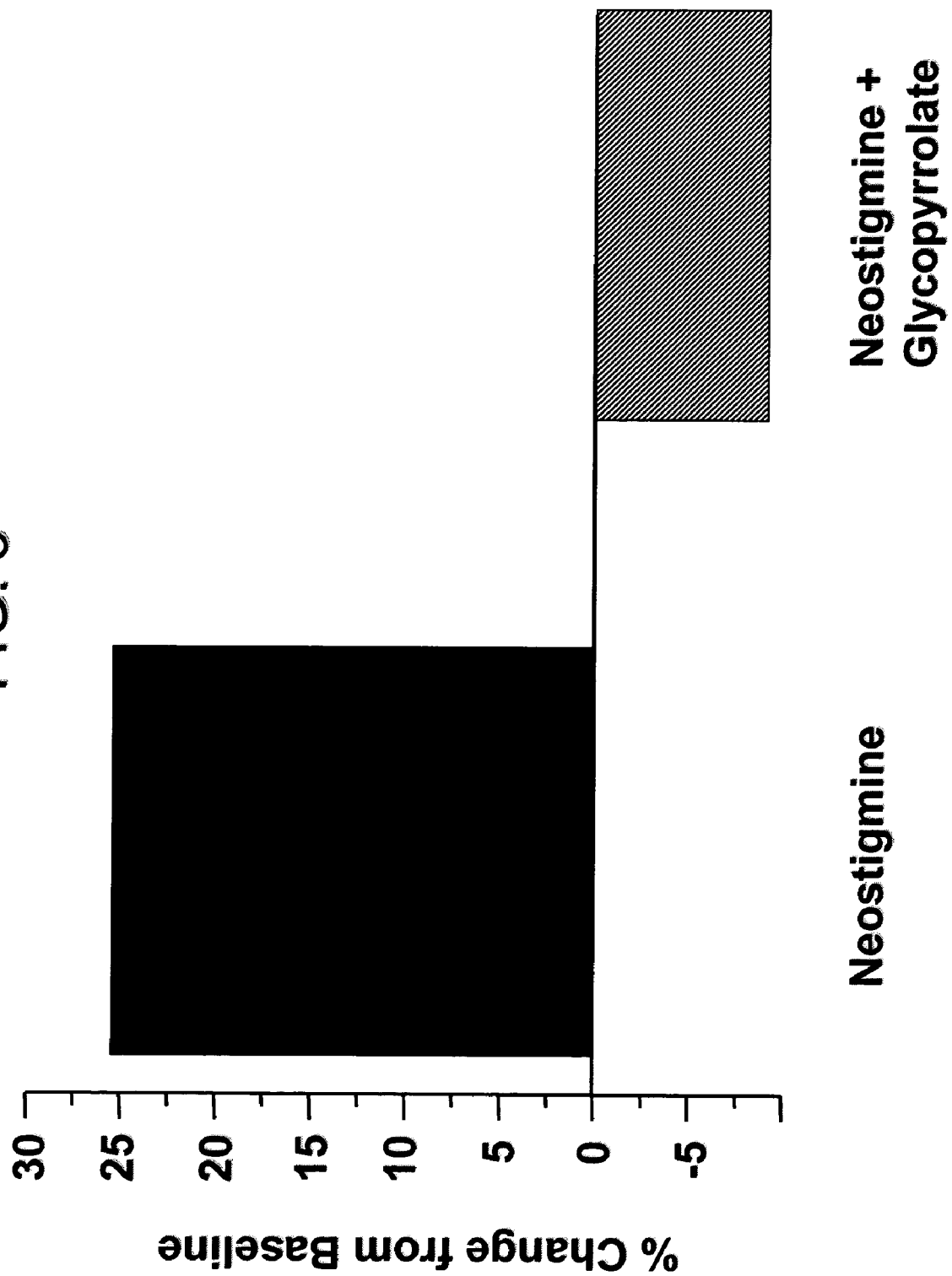
FIG. 8 shows a graph of the effects of 2 mg neostigmine (black bar) and a combination of 2 mg neostigmine and 0.4 mg glycopyrrolate (cross-hatched bar) on total airway resistance in thirteen paraplegic or quadriplegic subjects with DWE as measured by the forced oscillation technique using 5 Hz oscillations.
Figure 9:
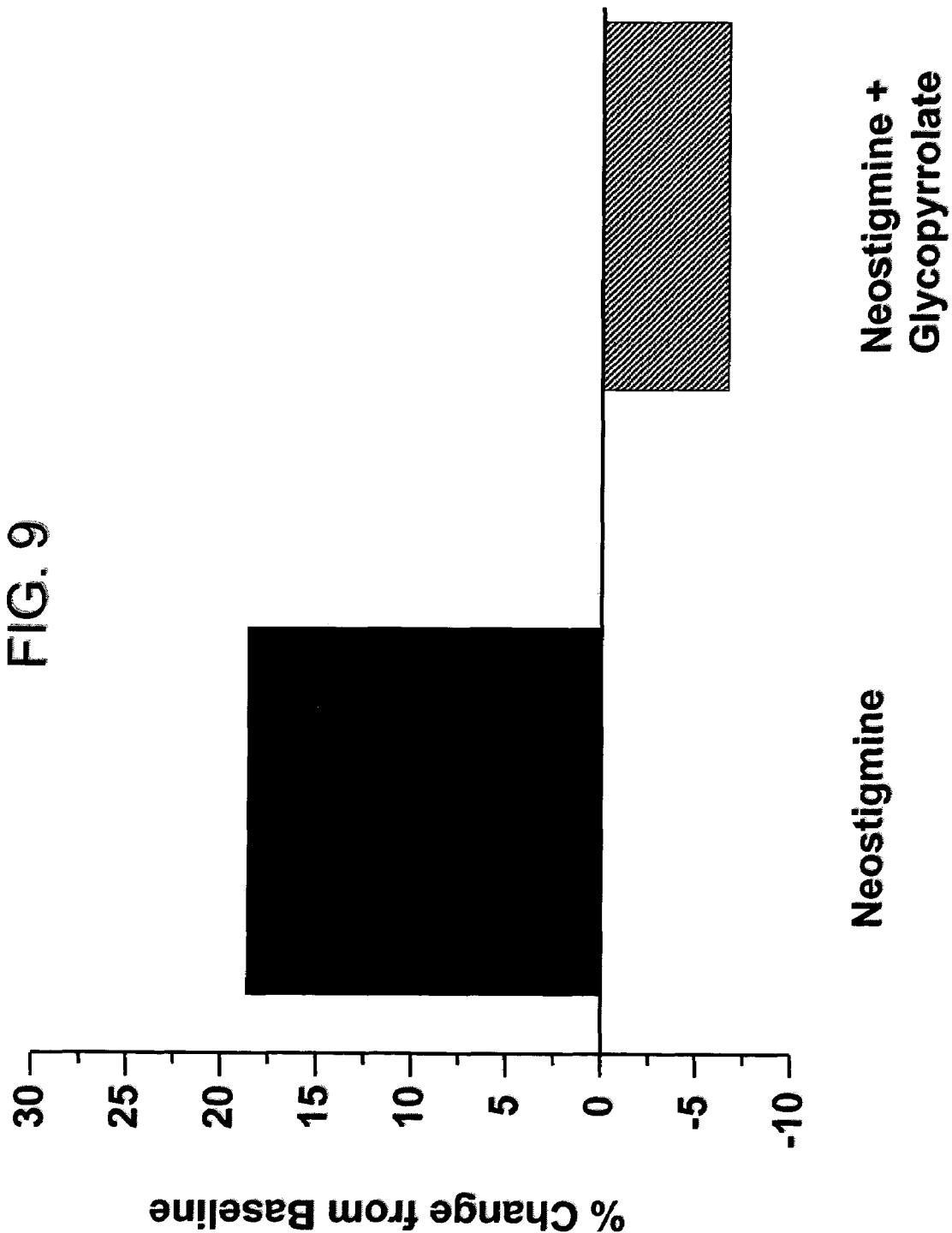
FIG. 9 shows a graph of the effects of 2 mg neostigmine (black bar) and a combination of 2 mg neostigmine and 0.4 mg glycopyrrolate (cross-hatched bar) on central airway resistance in thirteen paraplegic or quadriplegic subjects with DWE as measured by the forced oscillation technique using 20 Hz oscillations.

As shown in FIG. 8, total airway resistance increased approximately 25.5% over baseline upon administration of neostigmine alone. In comparison, total airway resistance decreased about 9% from baseline upon administration of the combination of neostigmine and glycopyrrolate. Similarly, FIG. 9 shows that central airway resistance increased approximately 18.4% over baseline upon administration of neostigmine alone. In comparison, central airway resistance decreased about 6.6% from baseline upon administration of the combination of neostigmine and glycopyrrolate. Taken together, these results indicate that administration of glycopyrrolate with neostigmine also counters respiratory side effects of neostigmine, such as bronchospasm. These results also indicate the usefulness of the drug combination for treatment of chronic intestinal pseudo-obstruction in patients with respiratory disorders, such as asthma.

This example demonstrates that (i) the colonic response to neostigmine is not blunted by glycopyrrolate; (ii) neostigmine alone or the combination of neostigmine and glycopyrrolate produced prompt and complete evacuation in 57% and 64% of subjects, respectively, (iii) the combination of neostigmine and glycopyrrolate caused less bradycardia than neostigmine alone, and (iv) glycopyrrolate counteracts the respiratory side effects caused by neostigmine alone.

Example 4

Repeated Administration of Neostigmine and Glycopyrrolate in SCI Subjects

This example demonstrates the use of a combination of neostigmine and glycopyrrolate for routine, on-going bowel care for spinal cord injured patients (including both paraplegic and quadriplegic subjects).

Subjects' baseline responses to the combination of neostigmine and glycopyrrolate for bowel care were determined as described in Example 2. Thereafter, subjects received periodic (2-3 times per week) intramuscular injections of 1-2 mg neostigmine and 0.2-0.4 mg glycopyrrolate. The 1 mg dose of neostigmine (with 0.2 mg glycopyrrolate) was used for subjects who had a complete evacuation of the oatmeal-barium bolus during the initial baseline treatment and the 2 mg dose of neostigmine (with 0.4 mg glycopyrrolate) was used for all other subjects.

Following administration of the drug combination, the subjects underwent their usual bowel care routines until satisfactory bowel evacuation was achieved. The treatments were continued for at least a month and are on-going.

Chronic administration of neostigmine and glycopyrrolate as described in this example decreased the bowel care time of the subjects by approximately 50-75% as compared to traditional methods of bowel care.

Example 5

Repeated Administration of Neostigmine and Glycopyrrolate in Rectal Suppository Formulation Formulation of Rectal Suppository The drug combinations disclosed herein, such as a combination of neostigmine and glycopyrrolate, are formulated with a suppository vehicle adapted for rectal administration. Methods of formulating rectal suppositories are well known in the art.

A typical rectal suppository includes a suppository base, certain adjuvenants and additives suitable for making such formulations. The suppository base may be an aqueous or a fatty base material, the latter being preferred mainly for ease of formulation and administration. Fatty base materials useful in a suppository base include, for example fatty oils and fats (such as, cocoa butter, palm oil, coconut oil, or lard), waxes (such as, lanolin and vasoline), or fatty acids (such as, oleic, stearic, and lauric acids).

The suppository preparations disclosed herein may also contain other additives, such as antioxidants (such as, butylated hydroxyanisole (BHA) or butylated hydroxytoluene (BHT)), stabilizers, viscosity builders, preservatives, and the like. The concentration of these additives may vary according to the particular additive used and the desired result sought. The use, the kind, and the concentration of additives for suppository preparations are within the knowledge of the ordinarily skilled artisan. In particular examples, agents may be added to promote the absorption of the active ingredients contained in the suppository (such as, a combination of neostigmine and glycopyrrolate) by the intestinal or rectal mucosa.

A combination of neostigmine and glycopyrrolate may be incorporated into the suppository vehicle using any method(s) known in the art. For example, neostigmine and glycopyrrolate may be incorporated into a suppository vehicle by the use of a buffer system, a gelatin stabilizer, or a bulking agent.

In some examples, a buffer system may be used as a carrier for a combination of neostigmine and glycopyrrolate. The buffer provides stability for the drugs and facilitates admixture with the components of the suppository vehicle. A representative buffer system may contain sodium or potassium phosphate/phosphoric acid buffer, or sodium or potassium acetate/acetic acid buffer, or sodium or potassium citrate/citric acid buffer. The concentration and pH of the buffer are preferably those values in which the drug combination is stable. For example, the concentration of the buffer may be in the range of 0.01 M to 0.5 M or in the range of 0.05 M to 0.2 M. A useful pH range for the buffer system is between 2 0 to 8.0.

In other examples, a stabilizer system may be used as a carrier for the combination of neostigmine and glycopyrrolate. A representative stabilizer system may contain from about 1 to about 32% w/w of a gelatin hydrolized in a 0.9% w/w sodium chloride solution or in purified water. A useful pH range for a stabilizer system is between 2.0 to 8.0.

In yet other examples, a lyophilized or dry mixed bulking agent may be used as a carrier for the combination of neostigmine and glycopyrrolate. Examples of bulking agents include, for example, gelatin, methionine, dextrose, sucrose, mannitol, sorbitol, lactose, methyl cellulose, povidone, sodium chloride and sodium acetate.

The components are the suppository may be combined, for example, by melting the suppository base with any absorption promoter, adding antioxidants and/or other additives, and adding a combination of neostigmine (e.g., 0.1-5.0 mg) and glycopyrrolate (e.g., 0.1-2.5 mg) suspended in a buffer solution or in a stabilizer system or homogenously distributed in a bulk powder mix. The mixture is blended and poured into suitable suppository molds and allowed to solidify.

Use of Rectal Suppository for Chronic, On-going Bowel Care

Subjects' baseline responses to the combination of neostigmine and glycopyrrolate in a rectal suppository formulation are determined as described in Example 2. Thereafter, a subject inserts (or has inserted by a home-care health care provider) a suppository into his or her rectum 2-3 times per week. Following insertion of the suppository, the subject will undergo his or her usual bowel care routine until satisfactory bowel evacuation is achieved. The treatments are continued for at least two weeks, but may continue for months, years, or until otherwise decided by the subject and/or his or her health care team.

Example 6

Repeated Administration of Neostigmine and Glycopyrrolate by Indwelling Catheter This example describes the chronic administration of a combination of neostigmine and glycopyrrolate by intravenous administration using an indwelling catheter, in particular a Port-A-Cath® catheter.

An indwelling catheter is tube that is implanted for a prolonged period of time (such as, weeks, months or years) with one end of the tube located within the body (such as, within a large vein) and the other end of the tube remaining accessible from the outside of the body. An indwelling catheter facilitates long-term intravenous drug therapy. Several types of indwelling catheters are known in the art, for example, the Port-A-Cath®, the Hickman catheter, and a PICC line (i.e., peripherally inserted central line). The Port-A-Cath® catheter is a well-known device having an injection port, which placed surgically under the skin of the arm or chest, and an attached catheter, which is inserted into a large vein in order to administer drugs to a subject. The Port-A-Cath® catheter is advantageous because it is less visible than the other types of indwelling catheters and it has less chance of infection because the injection port is located under the skin.

A subject with chronic intestinal pseudo-obstruction is identified as described herein; including, for example, spinal cord injured persons (such as paraplegic or quadriplegic persons). The subject's baseline responses to the combination of neostigmine and glycopyrrolate (in the amounts of 2 mg neostigmine plus 0.4 mg glycopyrrolate, or 1 mg neostigmine plus 0.2 mg glycopyrrolate) in an intravenous formulation are determined as described in Example 2.

Thereafter, the subject receives a subcutaneous port by implantation under general anesthesia. The surgeon makes a small incision in the chest where the subcutaneous portal is placed and another incision near the collarbone where the catheter enters a vein in the lower part of the neck. One end of the catheter is placed in the large blood vessel of the neck and threaded into the right atrium of the heart. The other end of the catheter is tunneled under the skin where it is attached to the portal. Fluid is injected into the portal to ensure that the device works properly. The portal is then placed under the skin in the right chest and stitched to the underlying muscle. Both incisions are then closed.

Once the implantation wounds have healed, the subject uses the indwelling catheter for intravenous injection of a combination of neostigmine and glycopyrrolate at the dosage determined to be appropriate in the initial examination. A topical anesthesia, such as EMLA cream or ethyl chloride, is applied to the skin above the portal prior to the needle poke. The subject or his or her health care provider inserts the needle of the syringe containing the drug combination into the subcutaneous injection port and administers the drug combination to the subject by injection. The injection port septum is self-sealing after needle removal, and is designed to withstand years of needle insertions.

Following administration of the drug combination, the subject undergoes his or her usual bowel care routine until satisfactory bowel evacuation is achieved. The treatments continue for at least two weeks, but may continue for months, years, or until otherwise decided by the subject and/or his or her health care team.

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims:

The invention claimed is:

1. A method of bowel care, comprising:
chronically administering intra-nasally a therapeutically effective amount of a drug combination comprising neostigmine and glycopyrrolate to a subject having chronic intestinal pseudo-obstruction to relieve chronic constipation, wherein the chronic intestinal pseudo-obstruction is a result of spinal cord injury and the ratio of neostigmine to glycopyrrolate is 2.5:1 to 10:1 by weight, thereby achieving bowel evacuation events without substantial bradycardia on a scheduled basis over a period of at least two weeks.

2. The method of claim 1, wherein the therapeutically effective amount of the drug combination is a ratio of neostigmine to glycopyrrolate of about 5:1 by weight.

3. The method of claim 1, wherein the spinal chord injury results in paraplegia or quadriplegia.

4. The method of claim 1, wherein neostigmine and glycopyrrolate are administered at about the same time.

5. The method of claim 1, wherein glycopyrrolate is administered about 1 to about 10 minutes after neostigmine.

6. The method of claim 1, wherein the method of administration is by a transnasal spray.

7. The method of claim 1, wherein the chronic administration occurs at least one time per week over a period of at least one month.

8. The method of claim 7, wherein the chronic administration occurs over a period of at least six months.

9. The method of claim 1, wherein the chronic administration occurs at least three times per week over a period of at least one month.

10. A method of bowel care for a subject comprising:
identifying a subject having chronic intestinal pseudo-obstruction as an effect of spinal cord injury; and
co-administering to the subject by a trans-nasal spray a therapeutically effective amount of a drug combination comprising neostigmine and glycopyrrolate at least one time per week for at least one month, wherein the ratio of neostigmine to glycopyrrolate is 2.5:1 to 10:1 by weight.

11. The method of claim 10, wherein the drug combination is chronically co-administered at least three times per week.

12. The method of claim 10, wherein the drug combination is chronically co-administered for at least six months.

13. The method of claim 10, wherein the identifying the subject having chronic intestinal pseudo-obstruction as an effect of spinal cord injury comprises selecting a subject who does not have acute-intestinal pseudo-obstruction.

* * * * *

UNITED STATES PATENT AND TRADEMARK OFFICE
CERTIFICATE OF CORRECTION

PATENT NO. : 7,635,709 B2
APPLICATION NO. : 10/672241
DATED : December 22, 2009
INVENTOR(S) : Korsten et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1218 days.

Signed and Sealed this

Ninth Day of November, 2010

David J. Kappos
*Director of the United States Patent and Trademark Office*